United States Patent [19]

Schoendorfer et al.

[11] Patent Number: 5,053,121
[45] Date of Patent: Oct. 1, 1991

[54] BLOOD CELL WASHING SYSTEMS AND METHODS

[75] Inventors: Donald W. Schoendorfer, Santa Ana; Lee H. Williamson, El Toro, both of Calif.

[73] Assignee: Baxter International Inc., Deerfield, Ill.

[21] Appl. No.: 443,550

[22] Filed: Nov. 29, 1989

Related U.S. Application Data

[63] Continuation-in-part of Ser. No. 159,446, Feb. 18, 1988, Pat. No. 4,919,817, which is a continuation of Ser. No. 895,505, Aug. 11, 1986, abandoned.

[51] Int. Cl.$^5$ .............................................. B01D 61/18
[52] U.S. Cl. .................................. 210/90; 210/321.64; 210/321.68
[58] Field of Search ............... 210/639, 651, 321.64, 210/321.68, 321.87, 335, 90, 360.1, 382, 96.2

[56] References Cited

U.S. PATENT DOCUMENTS 4,040,959 8/1977 Berman et al. .
4,605,503 8/1986 Bilstad et al. .
4,755,300 7/1989 Fischel et al. .
4,871,462 10/1989 Fischel et al. .................. 210/335 X
4,919,817 4/1990 Schoendorfer et al. ............ 210/639

FOREIGN PATENT DOCUMENTS

US82/00450 4/1982 PCT Int'l Appl. .

*Primary Examiner*—Frank Spear
*Attorney, Agent, or Firm*—June M. Bostich; Bruce M. Canter

[57] ABSTRACT

A system and method for cleaning contaminants from shed blood to enable reinfusion of a cell concentrate in the patient employs successive rotary membrane filtering stages in which Taylor vortices are generated. Shed blood led into the first rotary membrane stage is filtered to produce a hematocrit in the range of 50-60 with some of the waste matter being removed. The intermediate cell concentrate is passed to the second filter stage where further waste matter is initially extracted. At any intermediate region, however, a major amount of wash solution is fed into the concentrate and effectively mixed therein. In the remaining length of the second filter stage, waste matter is entrained in the wash solution and both waste and wash solution are filtered out to provide a cell concentrate from which the great majority of contaminants have been removed.

20 Claims, 4 Drawing Sheets

BLOOD CELL WASHING SYSTEMS AND METHODS

This application is a division of co-pending U.S. application Ser. No. 159,446, filed Feb. 18, 1988, now U.S. Pat. No. 4,919,817 which is a file wrapper continuation of U.S. application Ser. No. 895,505, filed on Aug. 11, 1986, now abandoned.

This application is related to the co-pending, commonly assigned applications Ser. No. 449,470, filed Dec. 13, 1982 of Halbert Fischel, and Ser. No. 591,925 filed Mar. 21, 1984, of Donald W. Schoendorfer. The present invention generally relates to method and apparatus for washing blood cells so as to permit reuse of same, such as by reinfusion to a patient's blood system.

BACKGROUND OF THE INVENTION

The first successful procedure for salvaging shed blood during an operation or emergency situation was used more than 150 years ago, in conjunction with reinfusion of blood to hemorrhaging women subsequent to child birth. This procedure, since termed autologous transfusion or autotransfusion, is now widely employed. The return of a patient's own blood is preferred to transfusion of blood from others because of biological compatibility. Autologous transfusion techniques include taking blood from a patient prior to surgery and returning it later during surgery as well as temporarily removing a quantity of whole blood and replacing it with isotonic solution. The latter procedure enables return of whole blood units to the patient after major surgery, with less cell damage from pumps artificial organ devices, such as an oxygenator, for example.

A number of systems have been developed over the last 20 years for use in autotransfusion applications. Some merely collect the blood, filter from it relatively large particle matter such as bone fragments from a traumatic incident, and return the blood under positive pressure to the patient. These systems are of limited applicability because they can neither concentrate the blood cells nor remove free hemoglobin, activated clotting factors or small cell debris.

Other autotransfusion machines, such as the "Cell Saver" of Haemonetics Corporation of Braintree, Mass., use centrifugation to both wash and concentrate salvaged blood. This product uses a batch processing approach and employs an expensive disposable, and therefore has limited flexibility while being of substantial cost. However, the washing removes a number of constituent factors which can adversely affect the patient, such as liberated red cell enzymes, activated clotting factors and anticoagulant, and concentrates the cells, so a higher quality blood mass is returned to the patient. Although this type of device represents the current state of the art in autotransfusion technology, its use in surgical procedures is limited because a large minimum volume of packed red cells is required for this batch process. The same problems exist with a centrifugal unit offered by Cobe Laboratories of Lakewood, Colo., but developed originally by IBM, for washing shed surgical blood. This unit is less expensive than the Haemonetics "Cell Saver" but much slower and more awkward to use. Both systems employ a saline solution for washing. A wholly different approach for autotransfusion, which apparently does not employ cell washing, is disclosed in U.S. Pat. No. 4,501,581 to Kurtz et al. In this system, primary attention is focused on deaerating the blood drawn into a collection chamber before forcing it back into the patient's circulatory system.

It is evident, therefore, that there is a need for a system that can concentrate blood cells, particularly for autologous transfusion, while also eliminating or minimizing the presence of activated substances and intracellular debris in the concentrate. The overall objectives are to return a high hematocrit concentrate to the patient (or to storage for later reinfusion), while minimizing the presence of adverse factors such as activated substances, intracellular debris, solid molecular waste and surgical solutions (anticoagulants, salines, etc). The system should, moreover, be capable of functioning in a wide variety of applications ranging from elective surgery to emergency surgery. Thus the system should be capable of functioning with different flow rates, volumes and condition of blood, and should utilize low cost disposables. Specifically, any disposable should be configured to be easily insertable into and removable from a machine without allowing contamination from one patient to be transmitted to another. It should also be so inexpensive as to introduce only a relatively low added cost to the procedure. And finally, it should operate on a real time, on-line basis, with sufficient versatility of operation to meet different conditions that may be encountered, such as a need for immediate return of shed blood to the patient.

More recently, superior systems for plasmapheresis, or the extraction of plasma from whole blood, have been disclosed in the above-referenced related patent applications of Halbert Fischel entitled "BLOOD FRACTIONATION SYSTEM AND METHOD", filed Dec. 13, 1982, Ser. No. 449,470, and of Donald W. Schoendorfer entitled "METHOD AND APPARATUS FOR SEPARATION OF MATTER FROM SUSPENSION", filed Mar. 21, 1984, Ser. No. 591,925. As described therein, blood passed into a gap between a rotating spinner and a relatively fixed wall, under proper conditions of gap size, spinner diameter, rotational velocity, and flow rates is believed to generate controlled and enhanced Taylor vortices within the gap. Consequently, matter, such as plasma, in the blood that is sized small enough to pass through the pores of a membrane on either the spinner or the shell will pass through the membrane at rates substantially in excess of those heretofore achieved under similar shear and flow rate levels. Fischel describes a cell washing application where an isotonic washing solution is passed through a porous fixed outer wall of the filter into the gap area. Schoendorfer describes the admission of rinsing solutions into the gap area at or in conjunction with the point of blood admission to the gap. Furthermore, even though the action can be continuous or intermittent, surface clogging and deposition phenomena are far less significant than in planar membrane systems. Where flow throughputs drop, moreover, the dynamic fluid conditions can be changed so as to aid in clearing the membrane as filtration continues. Systems utilizing this technology, such a the "Autopheresis-C" system of HemaScience Laboratories, Inc., operate very sensitively but stably with safeguards against the many factors that can affect patient comfort and safety.

SUMMARY OF THE INVENTION

Systems and methods in accordance with the invention pass shed blood in successive serial or concurrent parallel stages through different rotary membrane filtration systems, at least one of which introduces a washing solution intermediately for mixture with a concentrate. The stages employ Couette flow having enhanced Taylor vortices within a gap area disposed between relatively rotating generally cylindrical surfaces at least one of which includes a blood constituent filtering membrane. The most used mode is a serial one, in which sufficient non-cellular and waste matter is passed through the membrane of a first filtration unit to raise the hematocrit from its input level (e.g. 30) to the range of 50–60, despite variables that can exist in the blood being processed. An input stream of substantially controlled properties, but still containing some waste matter, is thus applied to the second filtration unit. Here the concentrate is again filtered, but it is also mixed with a larger amount of an isotonic solution that passes through the filter membrane, carrying with it dissolved molecular material and intracellular matter so as to achieve a final hematocrit in the range of 60–70 while having eliminated the great majority of waste material. The vortices established in the gap constantly sweep the membrane surface throughout its length, while concurrently mixing the isotonic solution with the shed blood in an extremely efficient fashion.

The same filtration units can alternatively be employed in the parallel mode, with or without substantial cell washing, in emergency and other special situations.

A more specific example of a system and method in accordance with the invention provides automatic control during different modes of operation. A pair of disposable units coupled serially by disposable tubing each utilize rotating spinners having covering filter membranes of less than about 1.2 micron pore size and internal passageways leading to coaxial waste outlets. The units are contained within small cylindrical housings that may be inserted readily into holders which rotate the spinners. Both filter units form biologically closed systems, and pressure transducers may be used to sense the transmembrane pressures therein for control purposes. Shed blood, after extraction of large particles in a gross filter, is stored in a cardiotomy reservoir, from which it is pumped to the first unit, with or without anticoagulant depending upon the operative procedure being used. Cell concentrate with some waste matter is pumped at the outlet end of the device to a pooling reservoir, while the major waste flow, having passed through the membrane, flows to a bag or reservoir. The second filtration unit is somewhat like the first, but also includes an input coupled into the gap between the membrane covered spinner and the shell at some spacing from the blood input end. A saline or other wash fluid is pumped and fed into this input at a rate approximately twice that of the partially filtered input concentrate as it is transferred from the pooling reservoir. Waste matter and the wash fluid are mixed thoroughly and filtered through the second membrane, exiting into the waste bag. The vortex action within th device very efficiently mixes the blood concentrate with the saline, which substantially lowers the viscosity of the concentrate and entrains waste matter within the saline flow. At the same time the vortex action and high shear rates in the system provide a very high permeate flux of waste and saline through the membrane. Blood cell concentrate having a hematocrit in the 60–70 range, but a very low percentage of waste matter, is passed to storage for reinfusion as needed.

This system therefore provides a low cost and easily assembled configuration of disposables which can operate in-line and in real time without requiring a significant minimum amount of blood. A feature of the invention is that efficiency of filtration in each device can be monitored in terms of the transmembrane pressure, and by the detection of hemoglobin in the waste matter. Depending upon dynamic conditions, therefore, flow rates can be controlled relative to blood characteristics, and the characteristics of the cell concentrate returned to the patient can be stabilized. The filtration is sufficiently thorough that 95% or more of all soluble elements, free hemoglobin, anticoagulant, and activated clotting factors are removed from the shed blood in producing the concentrated cells.

To operate the filtration units in parallel, with or without washing, only the blood and waste line couplings need be changed. This can be done, for example, to maximize the return of blood to the patient, where demanded by operating conditions.

BRIEF DESCRIPTION OF THE DRAWINGS

A better understanding of the invention may be had by reference to the following description, taken in conjunction with the accompanying drawings, in which.

DETAILED DESCRIPTION OF THE INVENTION

Systems in accordance with the invention, referring now to FIGS. 1 and 2, receive whole blood from a patient (during elective surgery or emergency procedures, or prior to surgery), and return concentrated red blood cells to the patient during concurrent or later surgery. The salvaged blood may be substantially damaged and will sometimes in emergency situations contain large foreign matter, such as bone chips, metal fragments, fat globules, or extraneous tissue. As much as possible of this extraneous material is extracted in a gross filter 12 having a 10 micron or larger pore size that passes all of the blood cellular matter. The blood is typically withdrawn from the patient by a pump 11 although in some instances gravity flow will suffice. After passage through the gross filter 12, the shed blood including waste matter is temporarily stored in a cardiotomy reservoir 14, which serves as a buffer to enable, at lease periodically, a continuous supply of shed blood to flow to the remainder of the system. A conventional level detector 16, which may use photosensitive, capacitive or mass measuring techniques, provides signals to a control system 20 that controls the time and sequence of operation of various driving mechanisms, and the direction of flow of fluids through the system. It is now common to use microprocessor-based systems, because of low cost and versatility, and because of ease of use. Many features of such a system are provided in the aforementioned "Autopheresis-C" system, but the present description, for simplicity and brevity, will be confined to sequencing and flow control functions.

A primary mode of operation of the system is as a cell concentrator and washer, in which a pair of Couette flow rotary filters 22, 24 are used serially. In this mode, a blood pump 28 extracts shed blood including waste from the cardiotomy reservoir 14 and transfers it through a valve or diverter 30 having a single input and a pair of outputs, only one of which is used in this mode. The shed blood is conducted from a first output to the input 32 of the first rotary filter 22. As described in the above-mentioned Schoendorfer application, the filter 22 includes a cylindrical rotary spinner 34 that is disposed within a outer cylinder 36 and covered by a filter membrane 37. The spinner 34 is rotated at a given rate by a motor 38 via a magnetic drive coupling 40. The gap between the spinner 34 and the shell 36, the diameter of the spinner 34 and the rotational velocity of the spinner 34 are selected, relative to the viscosity of the input suspension, to establish high shear across the membrane surface, and also to generate Taylor vortices in the suspension, as shown somewhat idealistically in FIG. 2 for filter 24. The Taylor vortices exist in the form of helical cells extending circumferentially about the surface of the spinner. They have an internal rotation within the cross section of the helices that causes the gap fluid to constantly sweep the surface of the membrane 32. The pore size of the membrane permits extraction of matter smaller than the pore size of the membrane (here approximately 0.8 microns although up to 1.2 microns may be used in some situations) into an internal passageway system (not shown) under the membrane that leads to an outlet 42 coaxial with the spinner 34. Concentrated cellular matter in the gap between the spinner 34 and the shell 36 moves to an outlet orifice 44 for ultimate transfer to the second rotary filter 24. As disclosed in the Schoendorfer application previously referenced, under stated conditions the membrane can be a stationary element positioned not on the spinner 34 but on the inner wall of the shell 36, with conduits leading filtrate out from the device. Both mechanisms function with high filtrate throughput per unit area of filter and are remarkable free of deposition and concentration polarization effects. However, it is preferred to employ the membrane on the spinner 34, inasmuch as this configuration is the one primarily employed for plasmapheresis applications, and because it appears to be better suited for the wide variety of conditions that may be encountered in elective and emergency surgery.

Superior control is also achieved by deriving a transmembrane pressure signal with a pressure transducer 46 coupled to the input of the first rotary filter 22, and providing a signal to the control system 20. The output side of the filter is maintained at substantially atmospheric pressure. By monitoring the transmembrane pressure in the filter 22 while precisely controlling pump flow rates, an accurate reading of the stability of operation of the filter can be obtained. Internal mechanisms within the blood which may activate clotting functions, or which may result in incipient clogging of the membrane, can thus be detected at an early stage and corrective measures taken.

The output 44 of the first rotary filter is coupled through a cell pump 50 and a diverter valve 88 to a pooling reservoir 52 which can be used as a buffer between the two filters 22, 24. A level detector 54 is employed to provide signals to the control system 20 to assure that the second rotary filter 24 is driven only when adequate matter is available in the reservoir 52. A cell input pump 56 transfers the once concentrated suspension from the pooling reservoir 52 to the input 58 of the second rotary filter 24. Concentrated washed cell output derived at an outlet 60 from the second filter 24 is fed, by washed cell pump 98 to a washed cell reservoir 62. Waste matter from the axial output 64 is directed to a waste reservoir 66, along with waste taken from the axial output 42 of the first rotary filter 22.

The second rotary filter 24 includes a cylindrical spinner 70 that is disposed within a cylindrical shell 72 and covered by a porous filter membrane 73. The spinner 70 is driven by a motor 74 via a magnetic drive coupling 76, while the filter 24 also receives, in an intermediate but carefully chosen region along the length of the spinner 70, an injected wash solution. Referring to FIG. 2 as well as FIG. 1, a wash fluid source 80 provides an isotonic solution, such as a saline solution, via a pump 82 to an injection port 84 that is coupled into the gap between the spinner 70 and the shell 72 about one-third of the distance along the length of the spinner 70 from inlet 58 toward outlet 60. The mixing of saline with concentrate is extremely effective as the cell mass moves through the filter 24 because the vigorous but non-traumatic vortex action constantly rotates matter within small cells that traverse regions adjacent the cell walls. The position of the saline input port is carefully chosen so that there is adequate additional prefiltration of the once filtered cell concentrate input to the second rotor, adequate rotor length to provide a mix zone to mix the saline rinse solution with the cell concentrate to in turn dilute the cells, and also adequate rotor length below this mix zone to finally reconcentrate the cellular matter. A position approximately 1" along a 3" long spinner is used in this specific example.

As in the first rotary filter 22, the transmembrane pressure in the second rotary filter 24 is sensed by a pressure transducer 86 coupled to the input and providing an output signal to the control system 20.

A second, alternative, mode of operation, which may be used in emergency situations or under particular conditions, should briefly be mentioned. In this mode the first and second rotary filters 22,24 are run in parallel, each functioning as a cell concentrator in order to return red blood cells to the patient at the maximum rate. In this situation, the switchable diverter 30, which has two output ports, is coupled to divide the input flow from the blood pump 28 into equal flows to the inputs to the two separate rotary filters 22, 24. A second diverter 88 coupled to the cell pump 50 directs output flow of concentrate from the first rotary filter 22 directly (via the dashed line flow) to the washed cell reservoir 62, along with the flow from the output 60 of the second rotary filter 24. In severe emergency situations the cellular components are not washed, and the saline input is not used in order to maximize the rate of cell reinfusion.

Figure 1:
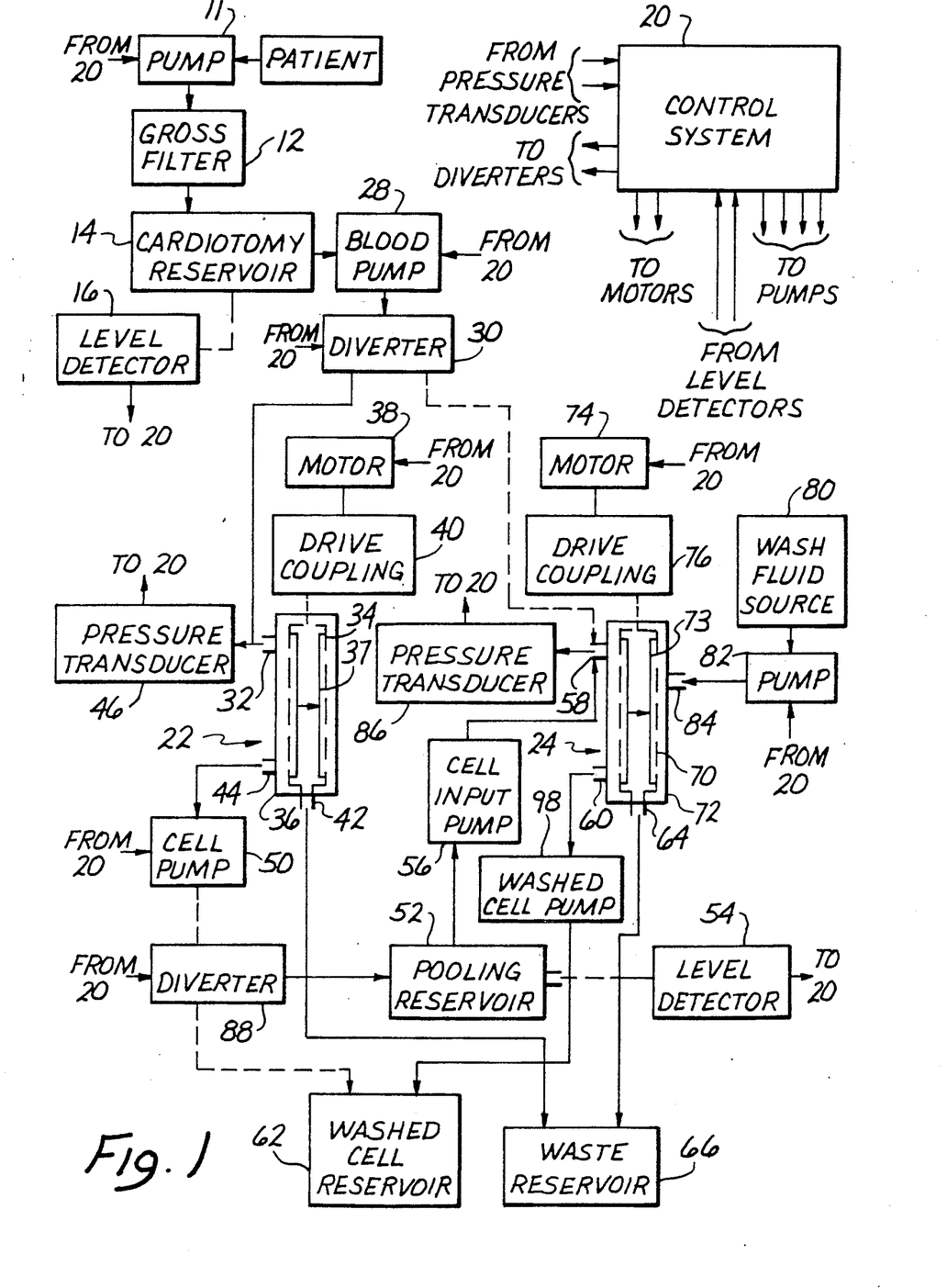
FIG. 1 is a block diagram representation of an exemplary autologous transfusion system in accordance with the invention.
Figure 2:
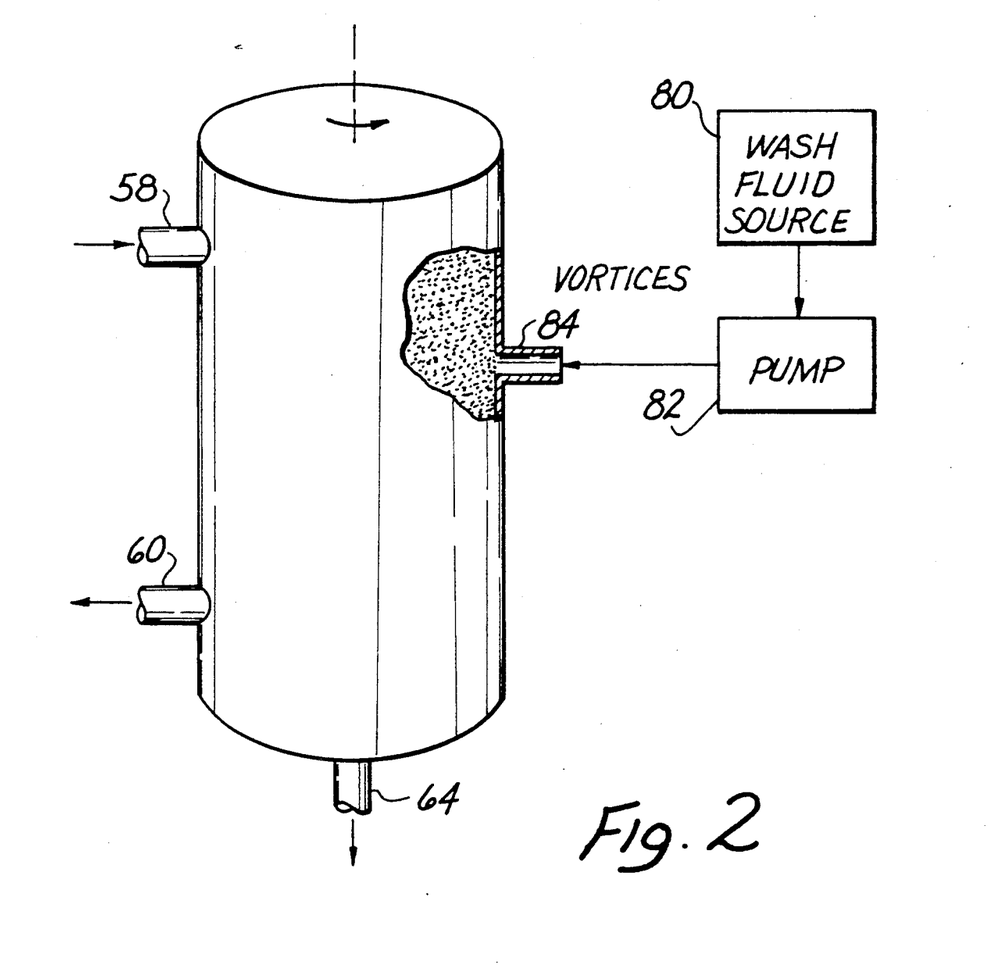
FIG. 2 is a perspective view, partially broken away, of a disposable filtering device used in the arrangement of FIG. 1.
Figure 3:
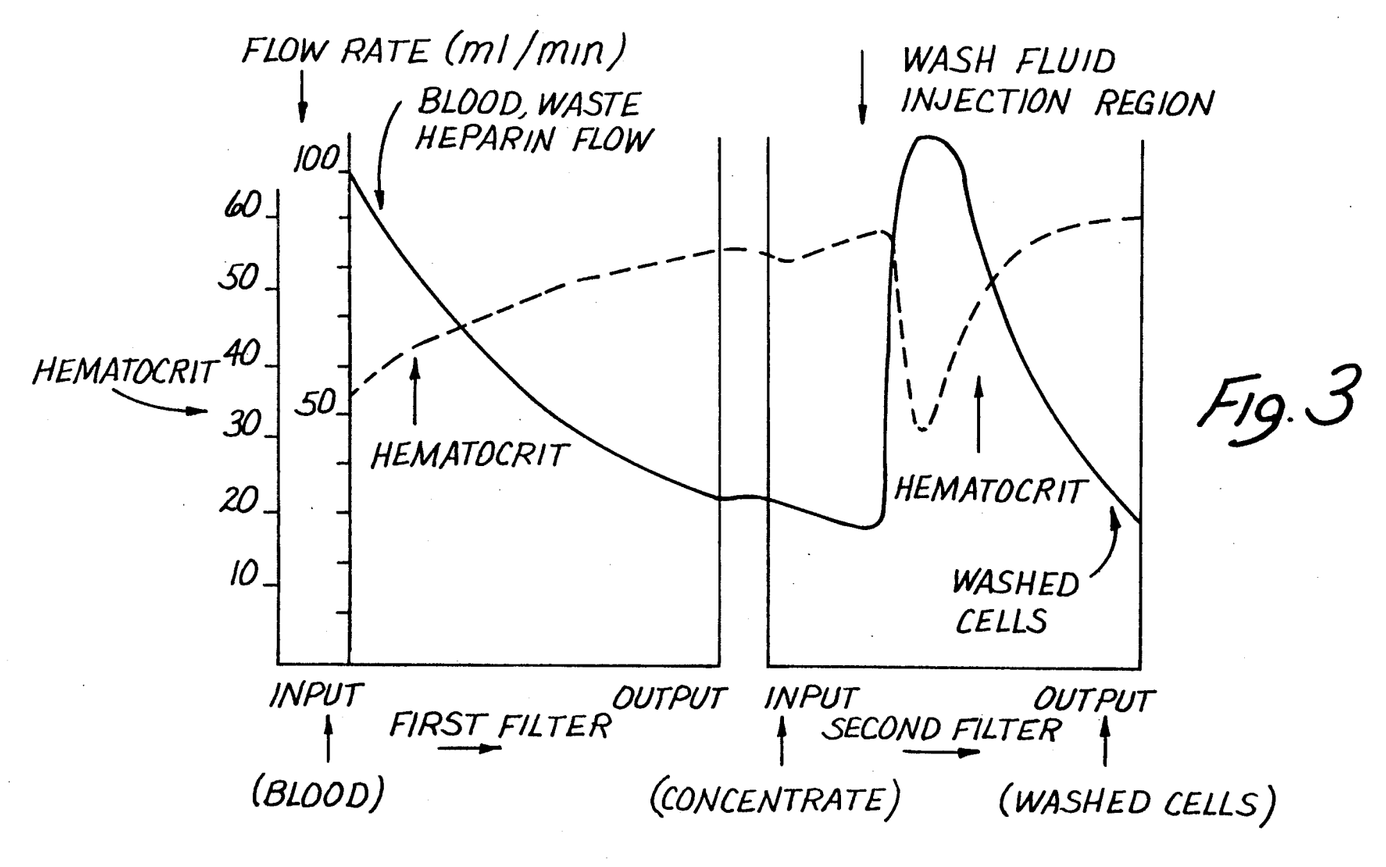
FIG. 3 is a curve showing the relationship between concentrate flow rates and concentrate hematocrit in a typical system in accordance with FIG. 1.

Referring to FIG. 3 as well as FIG. 1, the system in the most used mode of operation advantageously operates on the shed blood and waste input by first concentrating it to hematocrit levels in the range of 50-60, eliminating a substantial quantity of blood plasma and waste material but providing a mass of known viscosity and controllable characteristics to the second filter. In the second filter 24 the once concentrated blood, including waste is concentrated further. It is subjected again to enhanced vortex action with concurrent mixing of a major amount of isotonic solution, such that both waste and the dynamically mixed washing solution are extracted through the filter pores, leaving a suitably concentrated but thoroughly cleansed red blood cell concentrate having a hematocrit in the range of 60-70.

The use of a separate saline input port to the filter device 24 rather than merely mixing saline with the concentrated blood after the first device, and the optimized location of the saline input port are considered important design parameters which contribute significantly to the efficiency and cost effectiveness of the system. Another significant feature is the use of the first separator to process blood of variable conditions to a tightly controlled condition of concentration so that the second separator can operate efficiently. The dynamics of the system are carried out in real time, with what may be continuous operation but with what in most instances is a sequence of intermittent storage and processing steps consistent with the needs of the surgical procedure being undertaken.

In greater detail, the exemplary sequence proceeds as follows. With large particle matter in the shed blood having been eliminated in the gross filter 12, the shed blood including waste is accumulated in the cardiotomy reservoir 14 until a suitable level is detected by the detector 16 and control system 20. For most scheduled surgical procedures the blood will have been anticoagulated, as with heparin, and it will be desired to remove the anticoagulant as well as waste material. Whereas normal blood has a hematocrit in the range of about 37 to about 50, the shed blood, with cell damage, waste matter and heparin or other additives may typically have a hematocrit as much as about 10 points lower. With a predetermined minimum amount of blood detected in the reservoir 14, the blood pump 28 begins to feed the shed blood to the first rotary filter 22, which process continues until the content of the reservoir 14 has reached a certain minimum. Only in rare instances would the shed blood rate be greater than the input rate acceptable at the first rotary filter 22, and in such instances the system would typically be operated in parallel mode. In the typical case, however, waste matter, heparin and plasma passes through the axial outlet 42 via the pores of the filter membrane 37 on the spinner 34. At the same time, partially filtered concentrate is directed through the diverter 88 by th cell pump 50 into the pooling reservoir 52.

As depicted in graphical form in FIG. 3, a first rotary filter 22 having a 1" diameter and a 3" length, with a 3600 r.p.m. rate and a 0.025" gap, accepts an input flow rate of 100 ml/min and provides a concentrate flow of 30–40 ml/min and a waste and plasma output to the reservoir 66 of 60–70 ml/min. The decrease in concentrate flow rate is monotonic but not linear. The hematocrit in the concentrate correspondingly rises from its initial level, here about 35, to the range of 50–60, here about 55. The concentrate has a viscosity of 3–6 centipoises and may be pumped without difficulty or introduction of further hemolysis.

With sufficient concentrate accumulated in the pooling reservoir 52, as determined by signals from the level detector 54 applied to the control system 20, the second rotary filter 24 may be turned on, and the cell input pump 56 operated to provide input concentrate flow across the spinner 70 and the second rotary filter 24. At the upper end of the second spinner 70 there is a beneficial extraction of waste matter, the permeate flux in this region being greater than along the comparable length adjacent the output region of the first spinner 34. Thus there is an initial phase of removal of waste matter in the second unit, raising the hematocrit further and at a faster rate than did the immediately prior comparable length in the first filter. This increase in short term permeate flux may be due to lower back pressure, the influence of the saline introduced downstream, or other factors at this time is not fully understood.

Concurrently, or approximately at the time that the concentrate passes the wash fluid injection port 84, the pump 82 to the wash fluid source 80 is turned on, initiating a concurrent mixing and washing phase. The saline solution sharply increases the flow rate and entrains surgical saline, cardioplegic solution, small cell fragments and solid molecular wastes, including potentially activated materials. To a considerable extent, bacterial concentrations, such as might result from penetration of a portion of the intestine, are also entrained in the wash solution. With about 80 ml/min of saline added, the total flow rate in the gap adjacent the saline injection port 84 is about 110 ml/min. Because of the intense mixing action engendered by the Taylor vortices and the constant sweeping of matter in the vortices across the rotating filter membrane, such materials pass rapidly through the pores in the membrane. This action is extremely effective for washing the cells. The hematocrit of the concentrate moving to the outlet 60 and back to the wash cell reservoir 62 is brought up to the range of 60-70, here 65. A hematocrit of 70 is the approximate maximum desirable for transfusing the concentrate back into the patient. The waste material, anticoagulant and plasma are brought to low percentages, dependent of course on the initial level.

It will be noted that control of the product of the first membrane filtration may be of significant importance in controlling the ultimate concentrate, and that the interior mixing of the saline in a predetermined region (e.g. approximately one-third along the length of the secondary filter), together with the use of an approximately 2:1 ratio of saline to the first concentrate, are also significant in achieving the desired final result in the exemplary embodiment. The system is effective in eliminating 95% of all soluble elements, particularly those critical activated substances and intracellular contents that can precipitate clotting and potential harm to the recipient.

It will be appreciated that the flow rates of the first and second filters are inherently unlike, inasmuch as the 100 ml/min input flow rate is reduced to an output flow of about 40 ml/min in bringing the hematocrit from the range of 30 to 40 to about 50 to 60 in the first filter. Furthermore, the addition of saline in an approximately 2:1 ratio brings the total input flow rate for the second filter to a maximum of approximately 110 ml/min comprising 30-40 ml/min of partially concentrated cells and 70-80 ml/min of saline. This does not mean, however, that the second filter cannot keep up with the first. To the contrary, the filtrate flux at the second filter reaches high levels because of the uniformity, low viscosity and high proportion of saline input.

The aforementioned Schoendorfer patent application describes various control techniques for stabilizing and enhancing overall filtration action using transmembrane pressure as one of the gauges of operating performance. For example, in the event of an increase in transmembrane pressure, indicative of the incipient clogging of membrane pores, flow reductions may be undertaken to dislodge surface matter by the enhanced vortex action. In the present situation, two dynamic filtration systems are employed, and for given circumstances the rates may be adjusted to meet particular conditions, such as to stabilize the throughput of concentrate for a long period of time, or to achieve high return rates for short periods of time.

As previously noted, however, if an emergency situation arises in which a certain amount of cleansing action is required but the maximum rate of return of red blood cell concentrate is needed, then the flow diverter 30 feeds both filters 22, 24 in parallel, the wash fluid pump 82 is turned off, and concentrate outlets from both filters 22, 24 are directed to the cell reservoir 62, which in this situation does not contain washed cells.

Under a number of circumstances a single filtration with washing will suffice for removal of waste matter from shed blood. This may apply, for example, when there is a low volume of shed blood, low free hemoglobin and insubstantial amounts of anticoagulant. It is sufficient under such conditions to direct shed blood from the cardiotomy reservoir 14 through the blood pump 28 and diverter 30 directly to the input 58 to the second rotary filter 24. Using the given membrane covered spinner 70, with a 3 inch length and 1 inch diameter, blood input flow rates of 40 ml/min and wash fluid rates of approximately 80 ml/min provide a suitably purified red cell concentrate having a hematocrit of about 60.

Figure 4:
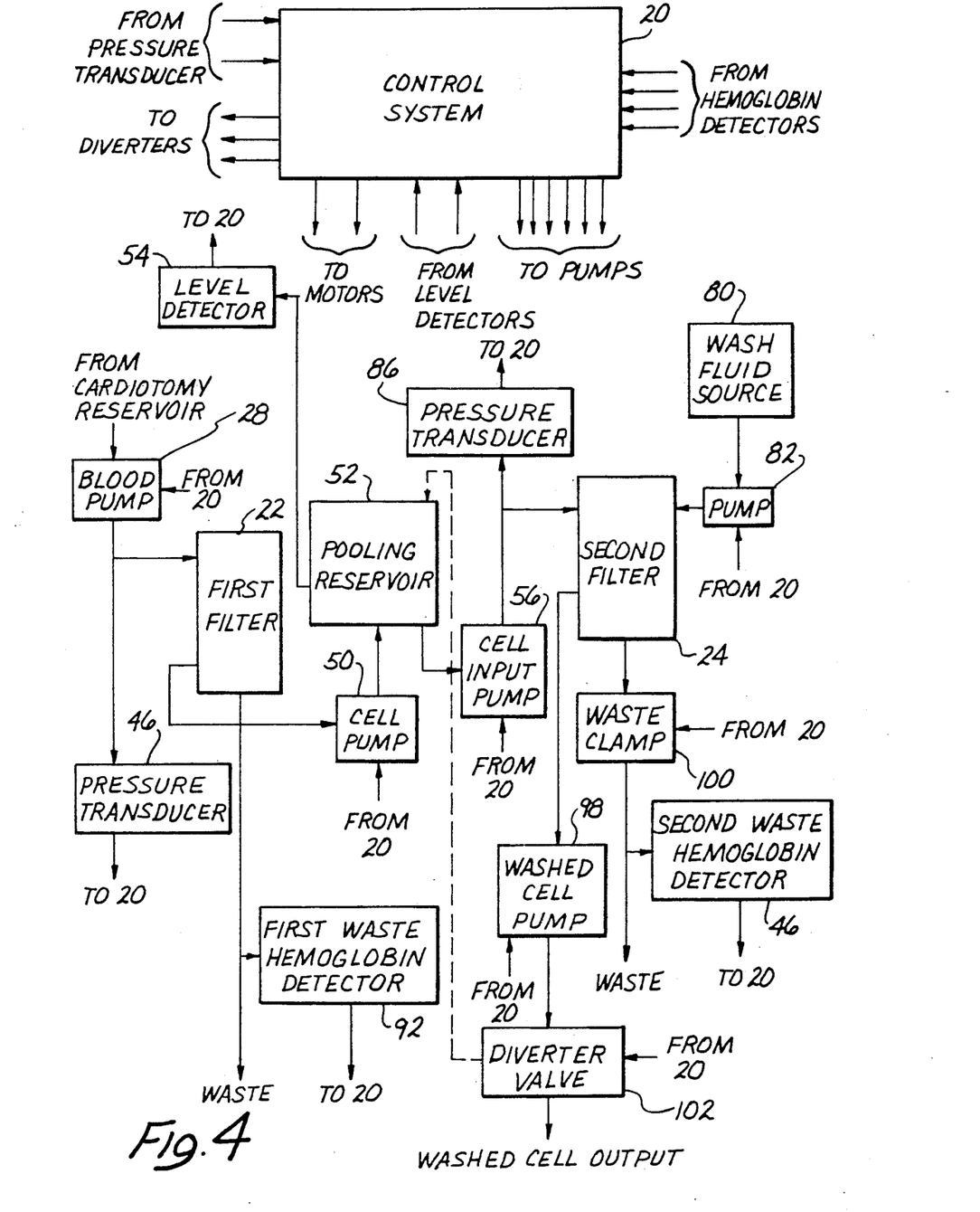
FIG. 4 is a block diagram of a modification of a portion of the system of FIG. 1.

The example of FIG. 4 depicts how a number of other modes of operation may be achieved in accordance with the invention. The system corresponds generally to that of FIG. 1, except, in part, for the incorporation of hemoglobin detectors 92 and 96 at the first filter 22 waste output, and the second filter 24 waste output, respectively. In addition the system includes a waste clamp 100 and a diverter valve 102 that is operable by the control system to return cell concentrate to the pooling reservoir 52. Both the hemoglobin detectors 92, 96 return signals indicative of hemoglobin content to the control system 20, and all the motors are variable speed devices (as is evident from the description of FIG. 1) that are controlled by the same system 20. Some elements and some component numbers have been omitted from FIG. 4 in the interest of brevity and simplicity.

The system of FIG. 4 can be utilized to effect manual or automatic control in a number of different modes. By sensing the hemoglobin percentage at the waste output of the first filter 22 with the hemoglobin detector 92, for example, it can be determined whether the free hemoglobin from the patient is within a predetermined acceptable range. If it is, then the control system 20 operates the second filter 24 in accordance with pre-established nominal conditions of flow and wash fluid input. If, however, the free hemoglobin in the waste is very low or below a predetermined range, then the control system 20 slows the pump 82 to decrease the wash fluid input rate from the source 80, because less washing is needed. Where free hemoglobin in the waste is high, above the predetermined range, further washing may be needed. For this purpose the rate of wash fluid input can be increased. However, if the limit of total flow rate for satisfactory washing is reached, the diverter valve 102 is switched for a period of time, causing the washed cell output from the second filter 24 to be directed back to the pooling reservoir 52. Thereafter, when the pooling reservoir is adequately full, the cell input is recycled through the second filter 24 as wash fluid continues to be injected, the diverter valve 102 at this time providing the washed cells as output. This recirculation procedure can be used as well in other difficult situations, where an immediate washed cell output is not required.

Furthermore, the system also has available additional control modes, based on the readings of transmembrane pressure derived at the pressure transducers 46, 86. If the transmembrane pressure at the first filter 22 increases above a given level, or rises too rapidly, filtrate flow rates can be reduced by accelerating the cell pump 50 to prevent clogging and facilitate clearing of the filter membrane 37.

At the second filter 24, the same expedient can be used but it can also be augmented by backflushing. Where filtration flow rates, established by the pump rates at the inputs and outputs are not commensurate with increasing transmembrane pressure, the cell input pump 56 may be slowed and the saline flow rate increased at the pump 82. The washed cell pump 98 is run at an increased rate after the filter passageways are substantially filled with saline, thus momentarily pulling waste material (mostly saline) back through the filter membrane 37, backflushing deposited material off the membrane and clearing the system. To further augment backflush all inputs to the second filter are arrested and waste clamp 100 of the waste output line is momentarily closed while the washed cell pump 95 is operated to create negative pressure which assists in the dislodgment of material such as foreign matter or blood cells from pores of the membrane filter 37.

The portions of the system illustrated in FIG. 1 and FIG. 4 that contact blood constituents are preferably formed of pressure disposable elements (e.g. plastic tubing, molded plastic parts assembled into connected filters, plastic reservoirs, etc.) which can be manually engaged with the active mechanical drivers, optical/pressure transducers, etc. For example, the tubing is inserted into engagement with conventional peristaltic pumps, a plastic reservoir is inserted adjacent an optical level detector, an end of the tubing may be fitted with a microbe filter and pneumatically coupled to a conventional pressure transducer, the plastic tubing may be passed through an optical sensor station for sensing hemoglobin in the filtrate, and the end of each filter may be engaged by a rotary magnetic coupled driver. A low cost, biologically closed system of low cost disposables may thus be used to implement all portions of the blood cell washing systems which come into contact with the biological fluids.

Although the system as described is most efficacious for use in the shed blood situation where all washed cell concentrate must be returned to a patient, it will be appreciated that the system may also be utilized in other situations in which washing may be of benefit. Blood cell concentrate stored in frozen form in an antifreeze solution may be comparably handled, using the first filter to adjust the hematocrit and the second filter and washing stage to assure complete removal of the antifreeze carrier.

Although various alternatives and modifications have been described above and illustrated in the drawings, it will be appreciated that the invention is not limited thereto but encompasses all forms and expedients within the scope of the appended claims.

We claim:

1. A system in which shed blood containing contaminants is processed to a red cell concentrate having reduced contaminants, said system comprising:

first filter means for receiving the shed blood and passing it longitudinally through a gap which extends adjacent a first filtration membrane of less than 1.2 micron pore size, the first filter means providing a filtered waste product and an intermediate cell concentrate product;

fluid flow control means receiving the intermediate cell concentrate product and providing a buffer supply thereof; and second filter means coupled to the fluid flow control means for receiving the intermediate cell concentrate product and passing it longitudinally through a gap which extends adjacent a second filtration membrane of less than 1.2 micron pore size, wherein the second filter means is for mixing a saline solution with the intermediate cell concentrate within the gap to provide a washed red cell concentrate.

2. The system as set forth in claim 1, wherein the first filter means provides an intermediate cell concentrate product having hematocrit in the range of 50-60 and the second filter means provides a washed red cell concentrate having hematocrit in the range of 60-70.

3. The system as set forth in claim 1, wherein the second filter means has an active length for filtering action and wherein the saline solution is added at an intermediate position along the active length.

4. The system as set forth in claim 3, wherein the first and second filter means each comprise rotating membrane means within a cylindrical shell and having diameters, interior spacing and rotational velocities selected to establish Taylor vortex flows within the gap without causing hemolysis therein, and means for extracting filtrate from the rotating membrane means.

5. The system as set forth in claim 4, wherein the second filter means includes:

spaced apart input and output cell fluid ports coupled to the interior spacing between the rotating membrane; and a saline solution input port longitudinally disposed between the input and output blood ports.

6. The system as set forth in claim 5 further including:

means providing controllable intermediate cell concentrate flow to the second filter means;

means providing controllable saline solution flow to the second filter means;

means for monitoring transmembrane pressure across the membrane in the second filter means; and means responsive to increases in the transmembrane pressure of the second filter means for controlling the blood flow and saline solution flow in the second filter means so as to backflush the filter membrane with saline solution.

7. The system as set forth in claim 6, wherein the system further includes:

a cardiotomy reservoir coupled to provide shed blood input to the first filter means;

hemoglobin detector means coupled to indicate the hemoglobin concentration in the filtrate from the first filter means; and means responsive to the detected hemoglobin indication for varying the flow rate of saline solution to the second filter means relative to an input flow of intermediate cell concentrate.

8. The system as set forth in claim 1, wherein the system further includes:

means for varying the flow rate of the saline solution so as to vary the washed red cell concentrate output flow rate.

9. The system as set forth in claim 1, wherein the system further includes:

means for controllably recirculating washed red cell concentrate through the second filter means.

10. The system as set forth in claim 1 further including:

means for alternatively directing shed blood through the first and second filter means in parallel.

11. The system set forth in claim 1, wherein said second filter means induces Taylor vortices within the gap to accelerate the mixing of said saline solution with said intermediate cell concentrate.

12. A disposable apparatus for use in washing and filtering blood constituents, said apparatus comprising:

a cardiotomy reservoir for temporary storage of input blood constituents;

a first rotatable filter coupled to receive fluid from said cardiotomy reservoir;

a pooling reservoir coupled to receive filtration concentrate from said first rotatable filter; and a second rotatable filter having an input coupled to receive filtration concentrate from said pooling reservoir, and having a washing solution inlet for receiving a washing solution and coupling the washing solution into mixing relationship with the received filtration concentrate.

13. The disposable apparatus as set forth in claim 12 further comprising:

a first controllable diverter valve disposed to selectably couple fluid between said cardiotomy reservoir and said first filter and between said cardiotomy reservoir and the input of said second filter; and a second controllable diverter valve disposed to selectably couple fluid between said first filter and said pooling reservoir and between said first filter and an alternate cell concentrate output line.

14. The disposable apparatus as set forth in claim 12 further comprising waste conduit means connected to collect and pass filtrate output from said first and second filters.

15. The system set forth in claim 12, wherein said second rotatable filter induces Taylor vortices within the gap to accelerate the mixing of said saline solution with said intermediate cell concentrate.

16. A disposable apparatus for use in washing and filtering blood constituents, said apparatus comprising:

a first rotatable filter having a fluid input for receiving blood to be washed and filtered, a filtrate output and a cell concentrate output;

a second rotatable filter having a fluid input, a filtrate output, a cell concentrate output and a washing liquid input disposed intermediate said fluid input and said cell concentrate output;

the cell concentrate output of said first filter being in fluid communication with the blood fluid input of the second filter.

17. The disposable apparatus as set forth in claim 16 wherein:

said first and second rotatable filters each comprise a longitudinally extending annular gap area between relatively rotatable generally cylindrical surfaces, at least one of which includes a blood constituent filtering membrane; and said washing fluid input is disposed relatively closer to the fluid input of the second filter than to the cell concentrate output thereof.

18. The system set forth in claim 16, wherein said second rotatable filter induces Taylor vortices within the gap to accelerate the mixing of said saline solution with said intermediate cell concentrate.

19. A blood constituent washing and filtering apparatus, comprising:
- a rotatable, generally cylindrical, blood constituent filtering membrane disposed within a stationary housing and defining a longitudinally extending annular gap therebetween in which Couette fluid flow, having Taylor vortices, can be established;
- a fluid inlet port to said gap;
- a fluid concentrate outlet port from said gap being longitudinally spaced apart from said fluid inlet port;
- a washing solution inlet port to said gap longitudinally disposed intermediate said fluid inlet port and said fluid concentrate port and closer to said fluid inlet port than to said fluid concentrate output port.

20. The system as set forth in claim 19, wherein said rotatable filtering membrane induces Taylor vortices within the gap to accelerate the mixing of said saline solution with said intermediate cell concentrate.

* * * * *